United States Patent [19]
de Louvencourt et al.

[11] Patent Number: 4,806,472
[45] Date of Patent: Feb. 21, 1989

[54] CLONING AND EXPRESSION VECTOR, YEAST TRANSFORMED BY SUCH VECTOR AND APPLICATIONS THEREOF

[75] Inventors: Laurence de Louvencourt, Levallois Perret; Hiroshi Fukuhara, Gif-sur-Yvette; Henri Heslot; Micheline Wesolowski, both of Paris, all of France

[73] Assignee: Societe Nationale Elf Aquitane, France

[21] Appl. No.: 945,164

[22] Filed: Dec. 22, 1986

Related U.S. Application Data

[63] Continuation of Ser. No. 576,382, filed as PCT FR83/00106 on Jun. 1, 1983, published as WO83/04261 on Dec. 8, 1983, abandoned.

[30] Foreign Application Priority Data

Jun. 2, 1982 [FR]   France .................................. 82 09564
Jun. 6, 1982 [FR]   France .................................. 82 15114

[51] Int. Cl.$^4$ ..................... C12P 21/00; C12N 15/00; C12N 5/00
[52] U.S. Cl. .................................. 435/68; 435/70; 435/910; 435/172.3; 435/255; 435/317; 435/320; 935/28; 935/37; 935/56; 935/69; 536/27

[58] Field of Search ................. 435/68, 70, 91, 172.3, 435/255, 317; 935/28, 37, 56, 60, 69

[56] References Cited

U.S. PATENT DOCUMENTS 4,418,150 11/1983 Gunge .............................. 435/256

OTHER PUBLICATIONS

Bach et al. (1979) *Proceedings National Academy Sciences*, USA vol. 76 pp. 386–390.
de Louvencourt, L. et al. May 1983 J. Bacteriol 154:737.
Struhl et al. (1979) P.N.A.S. 76:1035–1039.
Das et al. (1982) Curr. Genet. 6:123–128.
Niwa et al. (1981) J. Bact 148:988–990.

*Primary Examiner*—Thomas G. Wiseman
*Assistant Examiner*—Stephanie Seidman
*Attorney, Agent, or Firm*—Dressler, Goldsmith, Shore, Sutker & Milnamow, Ltd.

[57] ABSTRACT

Cloning and expression vector of a heterologous gene in a yeast, characterized in that it comprises at least; all or part of DNA of the plasmide $k_1$ of *Kluyveromyces lactis*, a DNA segment incorporating the heterologous gene as well as the sequences providing the expression of said gene in said yeast.

3 Claims, 2 Drawing Sheets

CLONING AND EXPRESSION VECTOR, YEAST TRANSFORMED BY SUCH VECTOR AND APPLICATIONS THEREOF

FIELD OF THE INVENTION

This application is a continuation of application Ser. No. 576,382, filed PCT FR83/00106 on June 1, 1983, published as WO83/04261 on Dec. 8, 1983, abandoned.

The present invention relates to novel cloning and expression vectors in yeasts, and to yeasts transformed with the aid of these vectors and their application in the synthesis of proteins.

Certain strains of yeasts of the species *Kluyveromyces lactis* contains a linear plasmid couple, the presence of which imparts "killer" character to the cell, this cell producing a toxin which prevents the growth of other so-called sensitive cells.

Sensitive cells which should be mentioned are the *K. lactis* cells deficient in plasmids, and also the cells of different species, such as *Saccharomyces cerevisiae*.

PRIOR ART

These plasmids were first described by Gunge et al. (J. Bacteriol. 145, 382–390 (1981), 147, 155–166 (1981), and independently by H. Fukuhara et al. (Current Genetics, in the press).

These are the two double-stranded linear DNA plasmids called $k_1$ (8.8 kb) and $k_2$ (13.4 kb).

The genetic studies carried out at the Laboratoire de M. Fukuhara reveal great analogy with the "killer" system of *S. cerevisiae*, except for the fact that the latter contains two RNA plasmids.

The plasmid $k_1$ is essential for expression of the "killer" character and of the immunity to the toxin, since the lack of this plasmid causes the disappearance of these two characteristics. It seems that the plasmid $k_2$ is necessary to maintain $k_1$ in the cell.

Replication of these DNAs involves several chromosomal genes of the yeast; the expression of the toxin also depends on nuclear genes. There are therefore interactions between the two plasmids and between the plasmids and the nucleus.

It has now been discovered that it is possible to use the plasmid $k_1$ as a cloning and expression vector.

DESCRIPTION OF THE INVENTION

The present invention thus proposes a cloning and expression vector of a heterologous gene in a yeast, which contains at least all or some of the DNA of the plasmid $k_1$ of *K. lactis*, a DNA segment incorporating the heterologous gene and sequences which ensure expression of the said gene in the said yeast.

The use of such a cloning and expression vector is of particular interest, firstly because few vectors which can be used in yeasts exist. In addition, the plasmid $k_1$ has several unique restriction sites, in particular EcoRI, BamHI and ClaI, which is of particular interest for the construction of recombinant hybrids.

Finally, it is known that the plasmids $k_1$ are present in a high copy number per cell, it being possible for this number of copies to reach 100 to 150. Under these conditions, it may be hoped that the gene which will be inserted in the vector will be amplified.

The heterologous genes are more particularly provided in the context of the present invention are genes which encode the synthesis of peptides or proteins of industrial interest.

In certain cases, the vector will of course contain various heterologous genes, some of which will not be expressed but of which certain sequences will ensure the expression of another gene.

Preferably, the gene to be cloned and expressed is inserted in one of the unique restriction sites, in particular in ClaI site.

It is of course possible, if this is advantageous, to insert in an appropriate site of the vector (that is to say in general downstream of the principal elements ensuring expression) a sequence containing multiple unique restriction sites as is known in this field, in order to be able conveniently to insert the heterologous genes.

Vectors according to the present invention which should be mentioned are those which incorporate, as the heterologist gene, the $URA_3$ gene of yeast, in particular in the form of a DNA segment of about 1.1 kb, limited by two HindIII sites.

Experiments have shown that integrality of the plasmid $k_1$ was not essential for cloning and expression. Thus, it was possible to use as the vector the plasmid $k_1\delta$, which originates from a "non-killer" mutant NK2 of *K. lactis* and is resistant to the toxin secreted. This plasmid $k_1\delta$ has a deletion of 2.9 kb, with respect to the plasmid $k_1$, between the two HindIII sites.

The vectors according to the invention can also contain bacterial DNA fragments, in particular bacterial DNA fragments containing an origin of replication and/or a gene having resistance to an antibiotic, the latter in particular to enable selection of the clones in the bacterial strains.

It is thus possible to insert a pBR322 restriction fragment containing the origin of replication and the ampicillin resistance gene.

The particular vectors according to the invention which are of special interest are circular plasmids such as pL3 which contains, as the DNA of plasmid $k_1$, a ClaI restriction fragment of the plasmid $k_1\delta$ and, in addition, preferably a ClaI restriction fragment of the clone 6 plasmid.

The various plasmids mentioned above can of course be prepared using known techniques.

The present invention also relates to the transformed yeasts incorporating a vector according to the present invention, and in particular, although not uniquely, strains of the genus Kluyveromyces, and especially *K. lactis*.

The invention also relates to the application of the transformed yeasts to the expression of the protein encoded by the heterologous gene carried by the vector.

Finally, the invention relates to a process for the preparation of a protein or a peptide, wherein a yeast transformed by a vector according to the invention containing, as the heterologous gene, the gene which encodes the said protein or the said peptide is grown on a nutrient medium.

DESCRIPTION OF THE DRAWINGS

The cloning and expression of the $URA_3$ gene of *S. cerevisiae* will be described below by way of example, with reference, where required, to the attached figures, in which.

I—CONSTRUCTION OF THE HYBRID PLASMIDS $k_1$-$URA_3$

The plasmids $k_1$ and $k_1\delta$ have already been described in the abovementioned articles.

Figure 1:
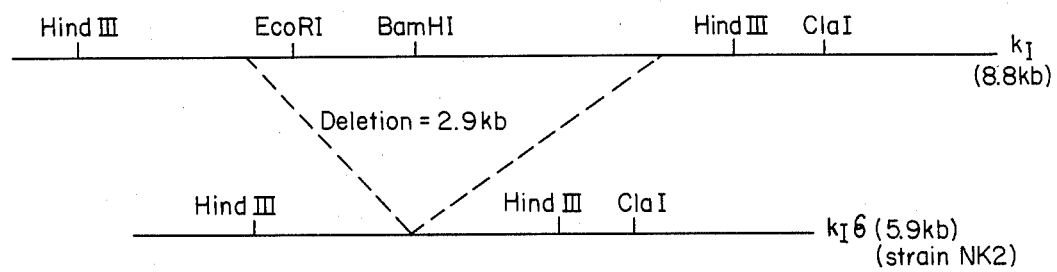
FIG. 1 represents plasmids $k_1$ and $k_1\delta$.
Figure 2:
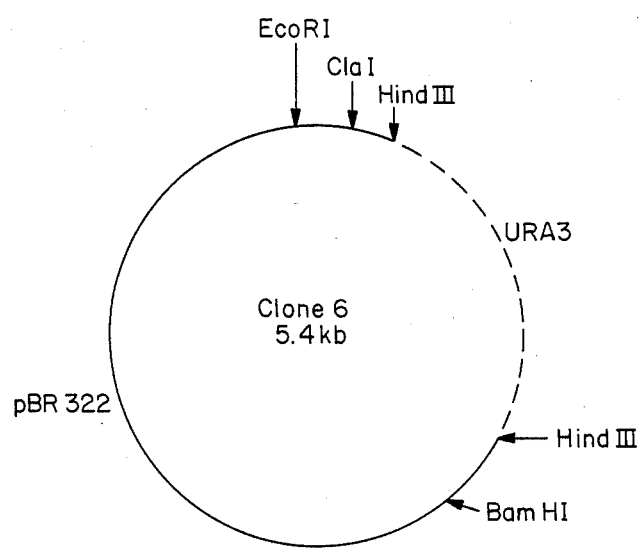
FIG. 2 represents the clone 6 plasmid
Figure 3:
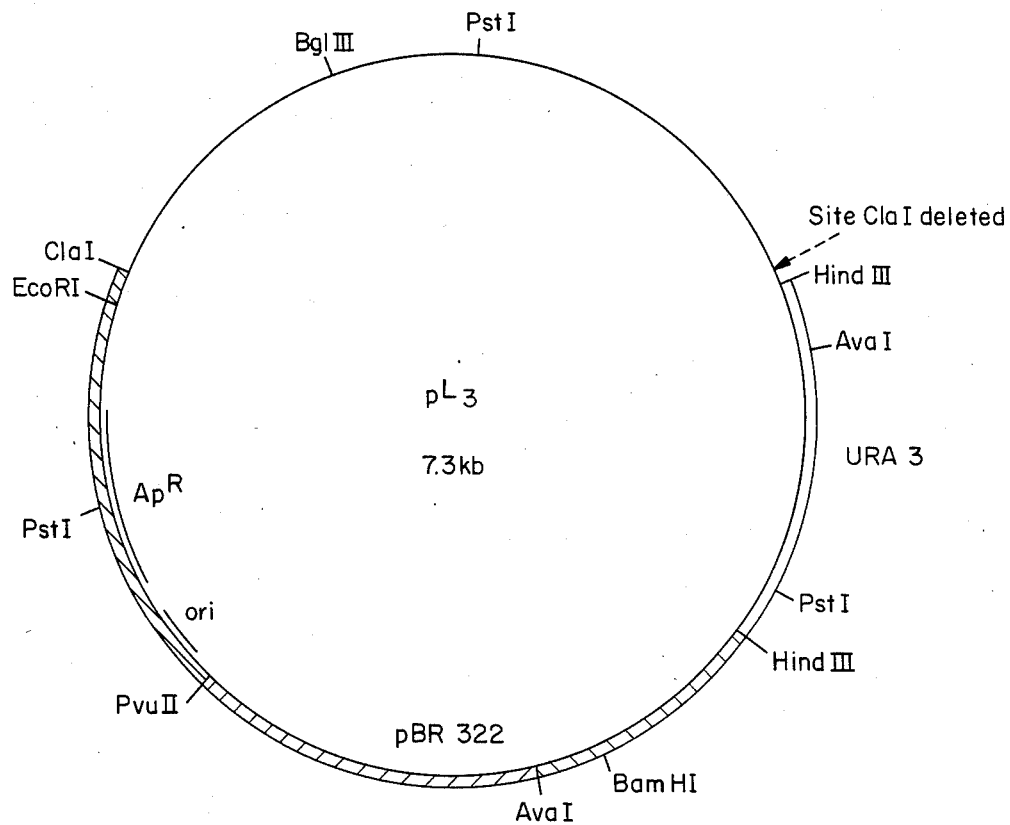
FIG. 3 represents plasmid pL3.

The restriction plan of plasmids $k_1$ and $k_1\delta$ has been shown in attached FIG. 1.

As can be seen, the plasmid $k_1$ carries three unique restriction sites, EcoRI, BamHI and ClaI, and carries a double restriction site, HindIII.

In contrast, plasmid $k_1\delta$, which carries a deletion of 2.9 kb, contains only a single unique restriction site, ClaI, but has preserved the two HindIII restriction sites.

This explains why, if cloning of a gene on the ClaI site is desired, it would be possible to effect total restriction, whilst if restriction effected by HindIII is desired, it would be appropriate to effect only partial restriction.

In order to avoid inactivation of a region necessary for replication, the marker $URA_3$ has been introduced in various sites of $k_1$ and $k_1\delta$.

First method of cloning: by HindIII

Partial restriction of the plasmids $k_1$ and $k_1\delta$ is effected by HindIII.

The $URA_3$ gene is obtained by total restriction of the clone 6 plasmid by HindIII (described by Bach et al., 1979, PNAS, 76, 386-390).

The whole $URA_3$ gene, carried by a DNA fragment of 1.1 kb, is thus obtained. This fragment is treated with alkaline phosphatase in order to prevent recircularization of the latter plasmid.

The following ligations are effected:
(1) $k_1$ cut by HindIII+clone 6 cut by HindIII,
(2) $k_1\delta$ cut by HindIII+clone 6 cut by HindIII.

Second method of cloning: by ClaI

Since the ClaI site is unique on the two plasmids used, that is to say $k_1\delta$ and clone 6, total restriction of the two plasmids may be effected.

The following ligation is effected:
(1) $k_1\delta$ cut by ClaI+clone 6 cut by ClaI.

The combination of these ligation mixtures contains a certain proportion of hybrid plasmids.

In order to be able to demonstrate cloning and expression of the $URA_3$ gene, it is appropriate to use a mutant strain of K. lactis, uraA−. In addition, in order to ensure that the vector according to the invention is maintained, it is useful for this receptor strain also to possess the plasmid $k_2$.

II—CONSTRUCTION OF A MUTANT STRAIN OF K. lactis urA−, WITHOUT $k_1$

The K. lactis CBS 2360-6 uraA− strain which has been depleted in OMP decase activity and has been obtained from the strain CBS 2360 by mutagenesis with UV, is used as the starting material.

The degree of reversion of the mutation is less than $1.10^{-8}$ cells.

This strain is "killer" and resistant to the toxin. It possesses the two plasmids $k_1$ and $k_2$ and is called ($k_1+$, $k_2+$).

The plasmid $k_1$ is eliminated from this strain by crossing with the "non-killer" strain VM2, which has been isolated by mutagenesis and has $K_1O$, $k_2+$ character.

The following crossing:

$$2360\text{-}6a\text{ ura}^- \times VM2\alpha Lys^-$$
$$(k_1+, k_2+) \quad (k_1O, k_2+)$$

leads to about 1% of diploid cells which have lost $k_1$ by mitotic segregation and have become "non-killer".

After sporulation of these diploid strains, a "non-killer" haploid strain ura− is obtained, for which it can be verified by extraction of the DNA that it has lost $k_1$ and still possesses $k_2$.

A "non-killer" strain uraA− ($K_1^O$, $K_2+$) has thus been obtained and will be used to demonstrate the expression of the gene cloned on the vector according to the present invention.

III—TRANSFORMATION OF K. lactis

The receptor strain constructed above is grown on a minimum medium (YNB 0.67%, glucose 2%) supplemented with uracil, up to a concentration of 1 to $2.10^8$ cells/ml.

After washing twice, the cells are suspended in a concentration of $10^9$ cells/ml in a protoplast formation buffer (0.6M KCl, pH 5).

Zymolyase 5000 (0.5 mg/ml) is added and protoplasts are obtained within 5 to 10 minutes at 34° C.

After washing twice, $2.10^8$ cells and 1 to 10 μg of DNA of the bonding mixtures are brought together.

2 ml of PEG 40% and 10 mM $CaCl_2$ are added and the mixture is left at the ambient temperature for 20 minutes.

After removal of the PEG, the mixture is incubated for 1 hour in a complete osmotically buffered medium; the protoplasts are included in the gelose by surfusion and are spread out on a minimum KCl medium.

The colonies appear after incubation at 30° C. for one week, and are small in size and, after subculture on minimum medium, many do not increase in size.

The efficiency of the transformation is one transformant per μg of DNA, and the degree of regeneration of the protoplasts is about 10%.

The results observed are as follows:

TABLE I

| Transformant DNA | Number of colonies per μg of DNA which increase in size after subculture | Name of the transformants | "Killer" resistant | Stability in selective medium (%) |
|---|---|---|---|---|
| $k_1\partial$ and clone 6 by Cla | 3 | L1 | "non-killer" sensitive | 0.13 |
|  |  | L2 | " | 35 |
|  |  | L3 | " | 28 |
| $k_1$ and clone 6 by Hind III | 4 | L4 | " | 35 |
|  |  | L5 | " | 61 |
|  |  | L6 | " | 1.5 |
|  |  | L7 | " | 0.5 |
| $k_1\partial$ and clone 6 by Hind III | 1 | L8 | " | 50 |

All the transformants given in Table 1 are UPA+, since they increase in size on a minimum medium without uracil. This shows that the URA3 gene of *S. cerevisiae* complements the uraA− mutation deficient in OMP decarboxylase of *K. lactis*.

The transformants thus obtained have different stabilities: when grown in minimum medium without uracil, between 40 and 99% of the ura− they segregate within 15 generations; when grown for the same number of generations on minimum medium+uracil, between 94 and 99% of the ura− they segregate.

It is, however, possible to stabilize the URA+ character by successive subcultures on minimum medium.

The presence of plasmids carrying $k_1$ and a foreign DNA, whether pBR322 or URA3, has been confirmed by the results of hybridization on gel or in situ.

By using three radioactive probes, that is to say $k_1$, pBR325 and URA3, it has been possible to show that: L4 carries a free plasmid of 4.4 kb, visible on gel, containing part of the $k_1$ and the URA3 gene; L3 carries a free plasmid of 9 kb containing part of the $k_1\delta$ and part of the DNA of pBR322.

The total DNA of the L2 and L3 transformants is extracted and this DNA is used to transform a pyr F strain of *E. coli* (mutation complemented by the URA3 gene of *S. cerevisiae*). The URA+ and Amp$^r$ transformants are then selected on suitable media, and transformants which have incorporated the plasmids according to the invention are obtained.

The extraction of the plasmids issued from the *E. coli* strains transformed by the DNA of L3 shows that these are plasmids conforming to the representation in the attached figure, these plasmids being called $p^L3$. These are circular plasmids which have a size of the order of 7.3 kb and possess a $k_1$ end cut by ClaI.

The attached figure shows the restriction plan of the plasmid $p^L3$, such as has been possible to determine by analysis.

This plasmid includes a bacterial fragment originating from the plasmid pBR 322 and a HindIII restriction fragment corresponding to the URA3+ gene of the yeast *S. cerevisiae* (these two DNA fragments originating from the restriction of the clone 6 plasmid by ClaI), and, finally, a ClaI restriction fragment of the plasmid $k_1\delta$ of *K. lactis*.

It is appropriate to note that in $p^L3$, as shown in the figure, one of the ClaI sites has disappeared in the vicinity of the DNA of the URA3 gene.

Under these conditions, the plasmid $p^L3$ comprises a large number of unique restriction sites: ClaI, EcoRI and BamHI, which makes it particularly suitable as a cloning vector for the gene in *K. lactis*.

In addition, this plasmid has the enormous advantage of being able to be amplified in *E. coli* and easily extracted, which makes it a particularly useful plasmid.

Finally, the plasmid $p^L3$ extracted from *E. coli* transforms the *K. lactis* ura− yeasts for ura+ character with an efficiency ten times greater than that obtained with the bonding mixtures such as is described in the main patent.

The procedures below are intended to illustrate the detailed preparation of vectors according to the invention, but without limiting the invention.

The strains

The *K. lactis* yeast strains used are: the wild strain CBS 2360 a ($k_1$+ $k_2$+), and the mutant CBS 2360 a uraA− obtained by induction with UV and deficient in OMP decase activity; and the strain VM2 $\alpha$lys− ($k_1^0$, $K_2$+) derived from the strain CBS 2359.

The *Escherichia coli* strain HB 101 Ap$^R$ Tet$_5^R$ containing the clone 6 plasmid carrying the URA3 fragment of *S. cerevisiae* of 1.1 kb.

The media

The yeasts are grown on minimum medium (2% of glucose, 0.67% of "yeast nitrogen base" Difco depleted in aminoacids, 2% of agar Difco). This medium can be supplemented by uracil (50 mg/liter) or lysine (40 mg/liter). The YPG medium contains 2% of glucose, 1% of yeast extract and 1% of bactopeptone. The crossing and sporulation medium is ME medium composed of 5% of malt extract and 2% of agar Difco. The "killer" test is carried out on GAL medium: 2% of galactose, 1% of bactopeptone, 1% of yeast extract, 0.05M $KH_2PO_4$ and 2% of agar.

Extraction of the plasmids

The extraction of the bacterial clone 6 plasmid is carried out in accordance with the method of Guerry et al. 1973 (J. Bact. 116, 1064–1066).

The extraction and purification of the plasmids of *K. lactis* were developed by M. Wesolowski, P. Dumazert and H. Fukuhara, 1982, Current Genetics (in the press).

The cells of a culture of 200 ml of YPG at the end of the exponential phase are washed once with water, weighed and suspended in 1M sorbitol (2 ml/g of cells) with zymolyase 60,000 (0.5 mg/g of cells).

After incubation at 30° C. for 45 minutes, the cells are centrifuged and suspended in a solution of 0.15M NaCl and 0.10M EDTA (2 ml/g of cells). 0.5 mg/g of cells of pronase and a final 1% of SDS are added.

After 1 hour of incubation at 37° C. and 1 hour at 50° C., the entire mixture is cooled and a final amount of 0.5M potassium acetate is added. The mixture is left in the cold for at least half an hour.

After centrifugation, the supernatant liquor is treated with RNase at 37° C. for half an hour. Sevag extraction (chloroform:isoamyl alcohol, 24:1, volume/volume) is followed by precipitation with ethanol (1.2 volumes).

The DNA strands collected with a Pasteur pipette are dissolved in TE (10 mM tris, 1 mM EDTA, pH 8). The DNA strands are reprecipitated with 0.56 volume of redistilled isopropanol and are redissolved in TE. This solution, to which a colorant (bromophenol blue) is added, is deposited on 0.6% agarose gel.

After migration at 60 V for 18 hours, the bands shown up by ethidium bromide which correspond to each plasmid are cut out. They are electro-eluted overnight at 100 mA.

The DNA is then introduced onto a DAEA-cellulose column and the column is washed with 0.3 to NaCl and eluted with 2M NaCl. The DNA is then subjected to CsCl gradient centrifugation, dialyzed and precipitated with ethanol.

Restrictions, ligations

The DNAs are restricted by restriction enzymes at 37° C. for 1 hour in the buffer corresponding to each enzyme. Partial restrictions are effected with a limiting amount of enzymes at 37° C. for 5 to 10 minutes.

Dephosphorylation is carried out at 60° C. for half an hour, with bacterial alkaline phosphatase.

Ligation is carried out after purification of the DNA with phenol and precipitation with alcohol, in the presence of the T4 DNA ligase at 10° C. overnight.

The transformation of *K. lactis*

We were inspired by the works of Hinnen et al. (1978) PNAS, 75, 1929-1933 and Gerbaud, Fournier, Blanc, Aigle, Heslot, Guérineau (1979) Gene 5, 233-253. The cells grown in minimum medium+uracil up to the exponential phase ($1-2.10^8$/ml) are washed once with distilled water and once with the protoplasticization buffer (0.6M KCl, pH 5).

The cells are resuspended at $10^9$ cells/ml in this buffer with 0.5 mg/ml of zymolyase 5000, and the suspension is incubated at 35° C. for a short time (5 to 10 minutes). More than 90% of protoplasts are obtained.

The protoplasts are washed twice with a buffer of tris HCl, pH 7.5, 0.6M KCl and 10 mM $CaCl_2$ by centrifuging at 1,800 g for 5 minutes and delicately resuspending the cells; they are concentrated to $10^9$ cells/ml in the latter buffer. 1 to 10 µg of ligation mixture are added to 0.2 ml of cells ($2.10^8$ cells) and the components are mixed well.

After incubation at the ambient temperature for 15 minutes, 2 ml of 30% strength (weight/volume) of PEG 4000 are added and the mixture is left at the ambient temperature for 15 minutes.

After centrifugation at 1,800 g for 6 minutes, the product is resuspended in 2 ml of 0.6M KCl, 6 g/liter of glucose, 6 g/liter of bactopeptone and 4 g/liter of yeast extract and the suspension is stirred gently at 30° C. for 1 hour.

The cells are then centrifuged and resuspended in 0.2 ml of the protoplasticization buffer. 5 ml of gelose are added, with surfusion at 46° C. (0.6M KCl, 2% of glucose, 0.67% of YNB "without aminoacids" Difco, 30 g/liter of agar Difco "purified" grade). The entire mixture is poured into a container which has been preheated at 55° C. and contains a mixture of the same composition as the above gelose but with a normal agar Difco.

Hybridization (1) Preparation of the hybridization filters on the colony (in situ) (Grünstein M. and Hogness D.S. (1975) PNAS 72, 3961-3965).

The colonies growing on W are replicated on a Schleicher and Schüll BA 85 filter placed on a container of W, and are incubated at 30° C. for 2 days.

Protoplasticization is effected at 30° C. in the course of half an hour with zymolyase 60,000 (1 mg/ml), in 0.6M KCl. After drying on Whatman paper, the filters are transferred successively to Whatman paper impregnated with: 0.5N NaOH (5 minutes), 1M tris HCl, pH 7.5 (2×2 minutes) and 1.5M NaCl and 0.5M tris HCl, pH 7.5 (2×5 minutes).

The filters are dried in vacuo at 80° C. for 3 hours.

(2) Hybridization on gel is carried out in accordance with the method of Southern E. M. (1975) J. mol. Biol. 98, 503-517.

(3) The filters are treated at 65° C. in various baths:

The prehybridization is effected in 3×SSC (20×SSC=3M NaCl, 0.3M Na citrate) for 30 minutes, then in the buffer of 3×SSC and 10×Denhardt (Denhardt=0.2% of Ficoll 400, 0.2% of bovine serum albumin and 0.2% of polyvinylpyrrolidone) for 3 hours and finally in the same buffer to which 50 µg/ml of the competitor DNA, 0.1% of SDS, 0.1M $NaH_2PO_4$, pH 5.6 and 10% of dextran sulfate have been added, for 2 hours.

For hybridization of the filters with the radioactive probe labelled at $^{32}P$ by nick translation, the denatured probe is added to the last bath of the prehybridization and is incubated at 65° C. overnight. Nick translation is described by Cameron et al. 1979, Cell, 16, 739-751, and in information from the Amersham Centre of Radiochemistry.

The first 6 washings of the filters are effected with 3×SSC, 10×Denhardt and 0.1% of SDS (with 50 µg/ml of the competitor DNA during just the first washing), and the last two washings are effected in 1×SSC. The filters are dried and recorded by Kodak films.

We claim:

1. A yeast from the genus Kluyveromyces transformed by a plasmid vector for expression of a heterologous protein in said yeast in which said vector is a circular plasmid comprising a portion of the DNA of the plasmid $k_1$ containing at least the replication sequence, a DNA sequence encoding a heterologous gene, and a DNA sequence which insures expression of the said gene in the yeast.

2. A yeast as claimed in claim 1 wherein the heterologous gene is the $URA_3$ gene of *S. cerevisiae*.

3. A method of preparing a protein encoded by a heterologous gene which comprises growing on a nutrient medium a yeast as claimed in claim 1.

* * * * *

UNITED STATES PATENT AND TRADEMARK OFFICE
CERTIFICATE OF CORRECTION

PATENT NO. : 4,806,472
DATED : February 21, 1989
INVENTOR(S) : Laurence de Louvencourt, Hiroshi Fukuhara, Henri Heslot and Micheline Wesolowski It is certified that error appears in the above-identified patent and that said Letters Patent is hereby corrected as shown below:

Column 1, line 65, "are" should be --, which are--

Column 2, line 17, "heterologist" should be --heterologous--

Column 2, line 20, "integrality" should be --integrity--

Column 3, line 51, "urA-" should be --ura A- --

Column 4, line 10, "$K_1O$" should be --$k_1O$--

Column 4, line 14, "2360-6a ura$^-$" should be --2360-6 a ura$^-$--

TABLE I, at the bottom of columns 3 and 4, second line under heading, at extreme left, "Cla" should be --Clal--

Column 6, line 2, "$K_2^+$" should be --$k_2^+$--

Column 6, line 53, "DAEA-cellulose" should be --DEAE-cellulose--

Signed and Sealed this

Twentieth Day of March, 1990

Attest:

JEFFREY M. SAMUELS

Attesting Officer

Acting Commissioner of Patents and Trademarks

UNITED STATES PATENT AND TRADEMARK OFFICE
CERTIFICATE OF CORRECTION

PATENT NO. : 4,806,472

DATED : February 21, 1989

INVENTOR(S) : Laurence de Louvencourt, Hiroshi Fukuhara, Henri Heslot, and Micheline Wesolowski It is certified that error appears in the above-identified patent and that said Letters Patent is hereby corrected as shown below:

Title page:
    Item ]73] on the cover page, "Aquitane" should be --Aquitaine--

Signed and Sealed this

Twenty-ninth Day of September, 1992

*Attest:*

DOUGLAS B. COMER

*Attesting Officer*      *Acting Commissioner of Patents and Trademarks*